United States Patent
Baker, Jr.

(10) Patent No.: US 8,690,770 B2
(45) Date of Patent: Apr. 8, 2014

(54) METHOD AND SYSTEM FOR DETERMINING WHEN TO REPOSITION A PHYSIOLOGICAL SENSOR

(75) Inventor: Clark R. Baker, Jr., Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 4 days.

(21) Appl. No.: 13/323,570

(22) Filed: Dec. 12, 2011

(65) Prior Publication Data

US 2012/0108912 A1    May 3, 2012

Related U.S. Application Data

(62) Division of application No. 11/240,441, filed on Sep. 29, 2005, now Pat. No. 8,092,379.

(51) Int. Cl.
*A61B 5/00* (2006.01)
*G06F 19/00* (2011.01)

(52) U.S. Cl.
CPC .................. *G06F 19/3406* (2013.01)
USPC ......................... 600/300; 600/323

(58) Field of Classification Search
USPC ........ 600/300–301, 323–324; 340/500, 573.1
See application file for complete search history.

(56) References Cited

U.S. PATENT DOCUMENTS

| | | | |
|---|---|---|---|
| 5,517,983 A * | 5/1996 | Deighan et al. | 128/204.23 |
| 5,774,425 A * | 6/1998 | Ivanov et al. | 368/11 |
| 6,014,346 A * | 1/2000 | Malone | 368/10 |
| 6,333,694 B2 * | 12/2001 | Pierce et al. | 340/573.1 |
| 6,346,886 B1 * | 2/2002 | De La Huerga | 340/573.1 |
| 6,384,728 B1 * | 5/2002 | Kanor et al. | 340/573.1 |
| 6,646,556 B1 * | 11/2003 | Smith et al. | 340/573.1 |
| 6,741,523 B1 * | 5/2004 | Bommarito et al. | 368/327 |
| 6,916,116 B2 * | 7/2005 | Diekmann et al. | 374/102 |
| 6,972,684 B2 * | 12/2005 | Copley | 340/573.4 |
| 7,027,358 B1 * | 4/2006 | Esposito et al. | 368/10 |
| 7,030,764 B2 | 4/2006 | Smith et al. | |
| 7,261,691 B1 * | 8/2007 | Asomani | 600/300 |
| 7,274,289 B2 * | 9/2007 | Kerr et al. | 340/500 |
| 7,289,016 B2 * | 10/2007 | Luebke et al. | 340/309.16 |
| 2001/0020898 A1 * | 9/2001 | Pierce et al. | 340/573.1 |
| 2002/0024443 A1 * | 2/2002 | Hawkins et al. | 340/573.1 |
| 2002/0084904 A1 * | 7/2002 | De La Huerga | 340/573.1 |
| 2004/0015132 A1 * | 1/2004 | Brown | 604/131 |
| 2004/0019258 A1 * | 1/2004 | Kavounas et al. | 600/300 |
| 2004/0059205 A1 * | 3/2004 | Carlson et al. | 600/310 |
| 2004/0102683 A1 * | 5/2004 | Khanuja et al. | 600/300 |
| 2004/0236199 A1 * | 11/2004 | Hawthorne et al. | 600/345 |
| 2005/0113653 A1 * | 5/2005 | Fox et al. | 600/300 |
| 2005/0128879 A1 * | 6/2005 | Sanford et al. | 368/109 |
| 2005/0185799 A1 | 8/2005 | Bertram | |
| 2005/0243655 A1 * | 11/2005 | McCutcheon et al. | 368/107 |
| 2006/0017559 A1 * | 1/2006 | Albert | 340/531 |
| 2006/0114754 A1 * | 6/2006 | MacDonald et al. | 368/327 |
| 2006/0200029 A1 * | 9/2006 | Evans et al. | 600/485 |

OTHER PUBLICATIONS

Skin Integrity Issues Associated with Pulse Oximetry; PA-PSPS Patient Safety Advisory, vol. 2, No. Jun. 2005.

\* cited by examiner

*Primary Examiner* — Bill Thomson
*Assistant Examiner* — Bobby Soriano

(57) ABSTRACT

A sensor may be placed on a patient to obtain physiological measurements. The application of the sensor on the patient may start a timer set to run for a given time interval. If the sensor is repositioned before the interval is expired, the timer is reset. If the time expires without the sensor being repositioned, a caregiver is prompted to reposition the sensor.

20 Claims, 2 Drawing Sheets

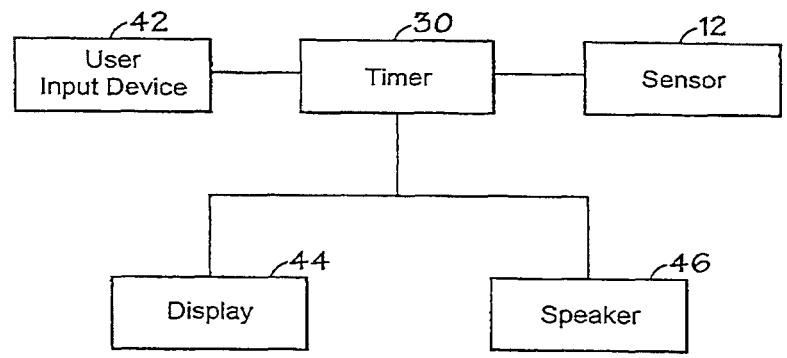
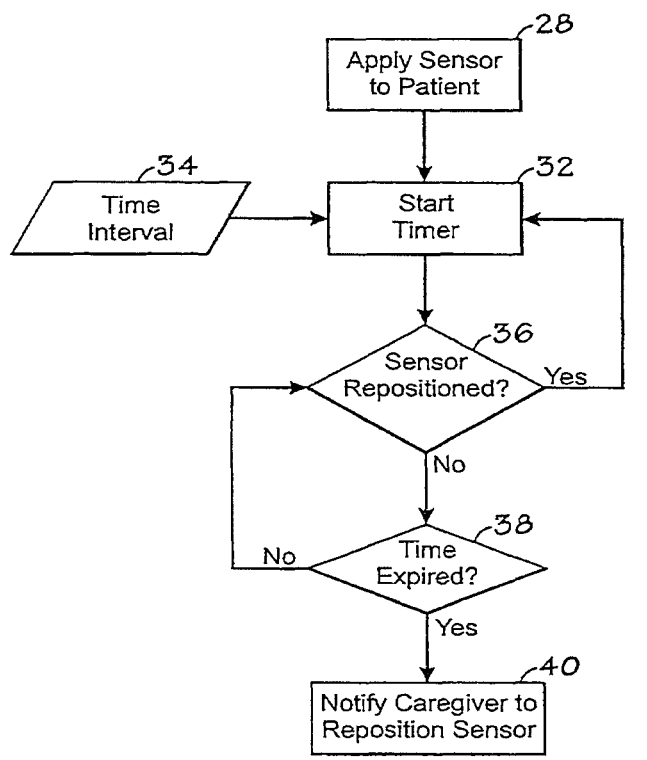
FIG. 2
FIG. 3

METHOD AND SYSTEM FOR DETERMINING WHEN TO REPOSITION A PHYSIOLOGICAL SENSOR

CROSS-REFERENCE TO RELATED APPLICATIONS

This application is a divisional of U.S. Pat. No. 8,092,379, entitled "Method and System for Determining when to Reposition a Physiological Sensor", filed Sep. 29, 2005, which is herein incorporated by reference in its entirety for all purposes.

BACKGROUND OF THE INVENTION

1. Field of the Invention

The present invention relates generally to medical devices and, more particularly, to the placement of sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of blood constituent in the tissue using various algorithms.

When applied to a digit or ear, it is generally desirable that the non-invasive sensor conform to the underlying tissue, fitting snugly. Such a snug fit helps exclude environmental or ambient light, which might otherwise produce incorrect or erroneous physiological data. The mild pressure associated with this snug fit, however, may be uncomfortable in some circumstances and/or may potentially compromise the accuracy of physiological measurements. Therefore, it may be desirable to reposition the sensor frequently, such as every four hours. However, doctors, nurses, and other health care providers may be unaware of the desirability to reposition the sensor frequently or may not remember when it is time to reposition the sensor.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for notifying an operator to reposition a sensor that includes: starting a timer upon application of a sensor to a patient, wherein the timer is set to run for a time interval; resetting the timer if the sensor is repositioned prior to the expiration of the time interval; and prompting a caregiver to reposition the sensor at the expiration of the time interval.

There is also provided one or more tangible machine-readable media that include: code adapted to start a timer upon application of a sensor to a patient, wherein the timer is set to run for a time interval; code adapted to reset the timer if the sensor is repositioned prior to the expiration of the time interval; and code adapted to prompt a caregiver to reposition the sensor at the expiration of the time interval.

There is also provided a physiological monitoring system that includes a sensor comprising at least one emitter and at least one detector; and a monitor comprising a timer set to run for a time interval and at least one of a display or speaker, wherein the timer is configured to start when the sensor is applied to a patient and to reset if the sensor is repositioned prior to the expiration of the time interval and wherein the at least one of a display or speaker is configured to provide a prompt if the sensor is not repositioned during the time interval.

There is also provided a method for starting a timer that includes: automatically determining if a sensor has been applied to a patient; and automatically starting a timer based upon a determination that the sensor has been applied to the patient.

There is also provided one or more tangible machine-readable media that include: code adapted to determine if a sensor has been applied to a patient; and code adapted to start a timer based upon a determination that the sensor has been applied to the patient.

There is also provided a physiological monitoring system that includes: a sensor comprising at least one emitter and at least one detector; and a monitor comprising a timer, wherein the timer is configured to automatically start based upon a determination that the sensor has been applied to the patient.

BRIEF DESCRIPTION OF THE DRAWINGS

Advantages of the invention may become apparent upon reading the following detailed description and upon reference to the drawings in which:

FIG. 2 illustrates components of an exemplary system for determining when to reposition a sensor, in accordance with aspects of the present technique; and FIG. 3 is a flowchart depicting exemplary actions for determining when to reposition a sensor, in accordance with aspects of the present technique.

DETAILED DESCRIPTION OF SPECIFIC EMBODIMENTS

Figure 1:
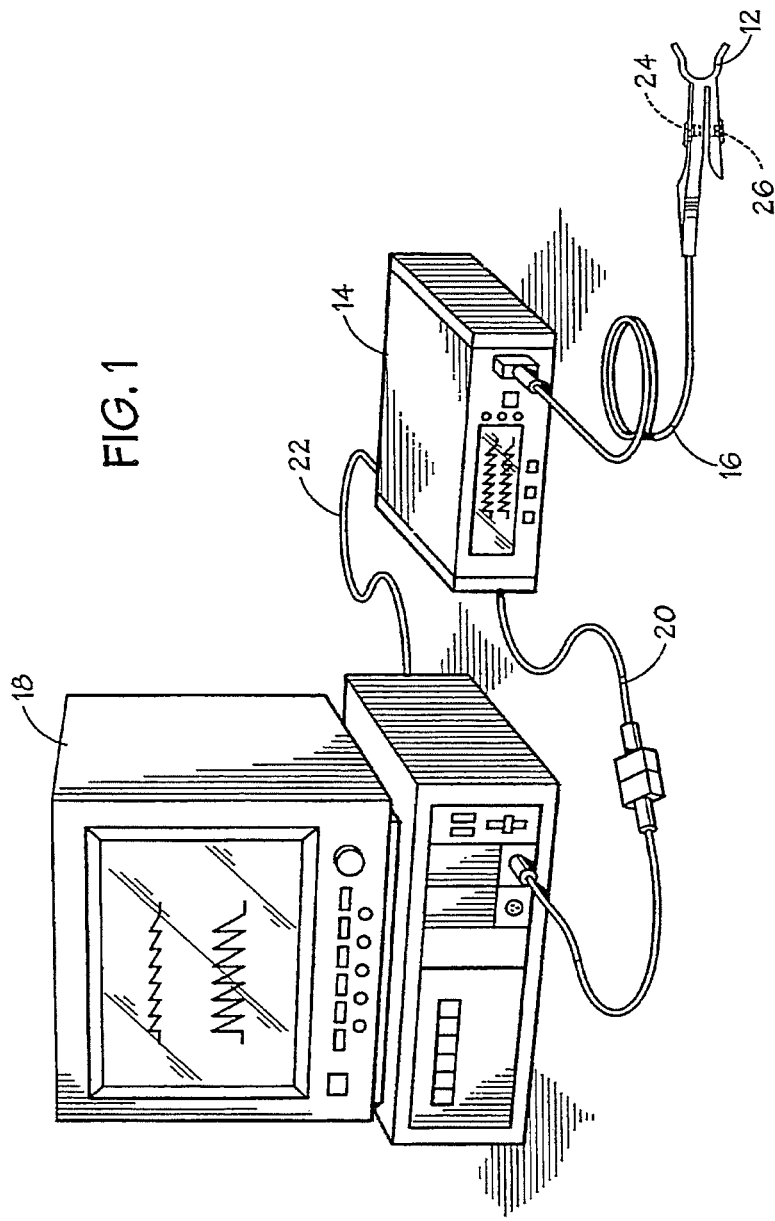
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In pulse oximetry and other spectrophotometric applications it is desirable to monitor the time interval a sensor has been applied to a patient and to notify an operator to reposition the sensor when appropriate. In accordance with some aspects of the present technique, a system is provided that is configured to time the duration a sensor is positioned on a patient and, if the sensor is not repositioned within a given interval, to notify an operator to reposition the sensor. The duration the sensor may remain in one position on the patient may be determined by the manufacturer of the sensor and/or the monitor or may be set by the best practices and procedures of a hospital or other health care facility at which the system and sensor are employed.

For example, referring now to FIG. 1, an exemplary patient monitoring system 10 for use in accordance with the present invention is depicted. The exemplary patient monitoring system 10 includes a sensor 12 used in conjunction with a patient monitor 14. In the depicted embodiment, a cable 16 connects the sensor 12 to the patient monitor 14. As will be appreciated by those of ordinary skill in the art, the sensor 12 and/or the cable 16 may include or incorporate one or more integrated circuit devices or electrical devices, such as a memory, processor chip, or resistor, that may facilitate or enhance communication between the sensor 12 and the patient monitor 14. Likewise the cable 16 may be an adaptor cable, with or without an integrated circuit or electrical device, for facilitating communication between the sensor 12 and various types of monitors, including older or newer versions of the patient monitor 14 or other physiological monitors. In other embodiments, the sensor 12 and the patient monitor 14 may communicate via wireless means, such as using radio, infrared, or optical signals. In such embodiments, a transmission device (not shown) may be connected to the sensor 12 to facilitate wireless transmission between the sensor 12 and the patient monitor 14. As will be appreciated by those of ordinary skill in the art, the cable 16 (or corresponding wireless transmissions) are typically used to transmit control or timing signals from the monitor 14 to the sensor 12 and/or to transmit acquired data from the sensor 12 to the monitor 14. In some embodiments, however, the cable 16 may be an optical fiber that allows optical signals to be conducted between the monitor 14 and the sensor 12.

In one embodiment, the patient monitor 14 may be a suitable pulse oximeter, such as those available from Nellcor Puritan Bennett Inc. In other embodiments, the patient monitor 14 may be a monitor suitable for measuring tissue water fractions, or other body fluid related metrics, using spectrophotometric or other techniques. Furthermore, the monitor 14 may be a multi-purpose monitor suitable for performing pulse oximetry and measurement of tissue water fraction, or other combinations of physiological and/or biochemical monitoring processes, using data acquired via the sensor 12. Furthermore, to upgrade conventional monitoring functions provided by the monitor 14 to provide additional functions, the patient monitor 14 may be coupled to a multi-parameter patient monitor 18 via a cable 20 connected to a sensor input port and/or via a cable 22 connected to a digital communication port.

As will be appreciated by those of ordinary skill in the art, the sensor 12 attached to the patient monitor 14 is typically placed on a patient in a location conducive to measurement of the desired physiological parameters. For example, a sensor 12 used for pulse oximetry is typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, or earlobes.

Where the sensor 12 is a pulse oximetry or other spectrophotometric sensor, the sensor 12 may be a "transmission type" or a "reflectance type" sensor.

Transmission type sensors include an emitter 24 and detector 26 that are typically placed on opposing sides of the sensor site. Reflectance type sensors, conversely, include an emitter 24 and detector 26 that are typically placed on same side of the sensor site. During operation, the emitter 24 shines one or more wavelengths of light toward the perfused tissue. The emitted light is received by the detector 26, either on the opposite side of the tissue in transmission mode or on the same side of the tissue in reflectance mode.

The light received by the detector 26 is processed to determine various physiological characteristics of the patient. For example, in pulse oximetry, the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500nm. In view of these example, it should be understood that, as used herein, the term "light" may refer not only to visible light, but to the electromagnetic spectrum in general, and may, therefore, include any wavelength within the infrared, ultraviolet, X-ray, gamma ray, millimeter wave, and microwave regions of the electromagnetic spectrum.

As noted above, it may be desirable to routinely reposition the sensor 12 on the patient. A system and technique to facilitate the routine repositioning of the sensor 12 is discussed with regard to FIGS. 2 and 3. In particular, functional components configured to perform the operations of the present technique are depicted in FIG. 2 while exemplary operations performed in accordance with the present technique are provided in FIG. 3. As will be appreciated by those of ordinary skill in the art, the various functional components and operations of FIGS. 2 and 3 may be associated with one or more of the devices described with regard to FIG. 1. For example, to the extent that a functional component of FIG. 2 performs its function via software (such as computer implemented routines or algorithms) and/or hardware (such as general or dedicated circuitry and/or user interface devices), either the patient monitor 14 and/or the multi-parameter monitor 18 may be a suitable platform for the respective functional component. Similarly, to the extent that an operation of FIG. 3 is performed by software and/or hardware, either the patient monitor 14 and/or the multi-parameter monitor 18 may include the respective software and/or hardware to perform the operation.

Referring now to FIGS. 2 and 3, a sensor 12 is applied to a patient (block 28). Upon application of the sensor 12, a timer 30 is started (block 32) which measures a set interval of time (block 34) within which the sensor 12 should be repositioned. If the sensor 12 is repositioned within the time interval 34, the timer 30 may be restarted (blocks 32 and 36). If the sensor 12 is not repositioned but the interval 34 has not yet expired, a continuing evaluation may be performed to determine if the sensor 12 is repositioned or if the interval 34 has expired (blocks 36 and 38). If, however, the sensor 12 has not been repositioned within the time interval 34 (blocks 36 and 38), a notification, such as an audible or visual indicator, may be provided to a caregiver to prompt the caregiver to reposition the sensor 12 (block 40). Upon reapplication of the sensor 12, the timer 30 may be reset and the process repeated.

As will be appreciated by those of ordinary skill in the art, the operations and functions described above may be accomplished by various means. For example, the functions of the timer 30 may be implemented by a conventional timing or timekeeping routine or algorithm, such as may be executed by processing or electronic components of the monitor 14 or 18. Alternatively, the functions of the timer 30 may be implemented by one or more dedicated circuits in the monitor 14 or 18 or by a combination of dedicated circuitry and routines. Likewise, the evaluation and notification functions described herein may also be performed by routines or algorithms executed by processing components of the monitors 14 or 18, by one or more dedicated circuits in the monitor 14 or 18, or by a combination of dedicated circuitry and routines.

With regard to the operation of the timer 30, an operator may start the timer 30 manually, such as via a user input device 42 of the monitor 14 or 18. Such a user input device 32 may include a button, dial, switch, key, or other mechanism on the monitor. Alternatively, the timer 30 may be started automatically, such as based on signals or data received from the sensor 12. In particular, a change in the light received by the detector 26 of the sensor 12 may be indicative of application of the sensor 12 to the patient and may, therefore, start the timer function. For example, a change, such as an increase or reduction, of light detected at the detector 26 may be indicative of application of the sensor 12. Such a change may be measured as a proportional change or as a change within a given unit of time. Similarly, the light detected may be evaluated in view of an absolute light threshold, with measurements on one side of the threshold indicative of an unapplied sensor and measurements on the other side of the threshold indicative of an applied sensor 12. Furthermore, only certain wavelengths of light, such as those wavelengths emitted by the emitter 24 may be used to evaluate application of the sensor 12. For example, the proportion of light received which is of the emitted wavelengths (or the relative absence of other wavelengths) may be used as an indicator of application of the sensor 12.

While light measurements are one mechanism by which sensor application may be evaluated, such as by the monitor 14 or 18, other mechanisms are also possible. For example, the receipt of valid data by the monitor 14 or 18, as determined by data evaluation routines executed by the respective monitor, may be used as an indication that the sensor 12 has been applied. Likewise, other measurements, if provided for by the sensor 12 and monitor 14 or 18 may be used to determine that the sensor 12 has been applied. For example, force or pressure sensors on the sensor 12 may be used as an indication that the sensor 12 is applied. Furthermore, other routines, algorithms, or techniques may be used to indicate whether the sensor 12 is or is not applied to the patient. For example, sensors and monitors employing neural networks and input metrics to determine a sensor ON/OFF state, as described in U.S. Pat. No. 6,035,223, hereby incorporated herein by reference, as well as other sensor ON/OFF indication techniques may be used in accordance with the present invention to indicate the application of the sensor 12 to the patient and the corresponding start of the timer 30.

The interval 34 (such as a 1, 2, or 4 hour interval) measured by the timer 30 may be set by the manufacturer of the sensor 12 or the monitor 14 or 18 based on the manufacturer's assessment of the best practices for use with their devices. For example, in one embodiment, the interval 34 is determined based upon the type of sensor 12 employed with the monitor 14. In such an embodiment, the sensor 12 or associated cable 16 may include an integrated circuit device, such as a memory device, which contains the time interval 34 itself or information (such as a model number) that may be used to ascertain the interval 34, such as via a look up table on the monitor 14.

Alternatively, the time interval 34 may be established by the hospital, clinic, or other health care facility to correspond to the facility's institutional practice or guidelines. Similarly, a supervising doctor, a nurse, or another health care provider may establish the interval 34 based on personal preference, established practice, or patient specific circumstances. In embodiments where the facility or health care provider set the interval 34, the interval 34 may be set via hardware and/or software provided on the monitor 14. For example, the interval 34 may be set by selecting the desired time interval from a menu provided on a display of the monitor 14 or by selecting the interval 34 via a user input device provided on the monitor 14.

In the event that a caregiver is to be notified to reposition the sensor 12 (block 40), the notification may be provided in various ways. For example, a visual prompt (such as a blinking light, a color coded symbol, and/or a beeping alarm) may be provided to the caregiver via a display 44 on the respective monitor. In addition, visual prompts may include alphanumeric or text messages provided on the display 44 requesting that the caregiver reposition the sensor 12. Alternatively, the routine visual indicators of the measured physiological parameter(s) may be modified to prompt the caregiver. For example, a numeric or other indicator of the measured physiological parameter may be alternated with the display of other, non-numeric characters, such as dashes, asterisks, punctuation characters, and so forth, to prompt action by the caregiver. Similarly, the numeric or other indicator of the measured physiological parameter may be displayed using a different font and/or font size than is normally used or may be displayed with emphasis, such as in italics, underlined, in bold and so forth.

Similarly the caregiver may be notified to reposition the sensor 12 (block 40) by an audible prompt provided via a speaker 46 internal or external to the respective monitor. Audible prompts may include verbal instructions or messages played on the speaker 46 in addition to or instead of displaying a visual prompt. Alternatively, the routine audible indicators generated by the respective monitor may be modified to prompt the caregiver. For example, an exemplary audible indicator may be a beep tone, such as a beep tone in which each beep corresponds to a measured pulse. Such a beep tone (or other respective audible indicator), may be modified by changing a beep characteristic (such as tone, pitch, and/or volume), by turning off the beep tone, and/or by skipping beeps, such as every second, third, or fourth beep.

Similarly, in some embodiments, the physiological data being measured, such as pulse oximetry data or tissue water fraction, may not be displayed or may be displayed in only a limited manner to notify the caregiver to reposition the sensor 12 at block 40. For example, measured physiological data, such as blood oxygen levels and/or pulse rate, may not be displayed on the monitor 14 or 18 until the sensor 12 is repositioned and the timer 30 restarted. In such embodiments, provisions may be made to display the measured physiological data in the event that the data is outside of an expected or desired range, however, routine measurements used for monitoring may be withheld to notify the caregiver that the sensor 12 should be repositioned.

In addition, the notification indicated at block 40 may be graduated or scaled based upon the extent by which the interval 34 has been exceeded. For example, a visual and/or audible prompt, such as a blinking light and/or alarm beep may be initially provided at the expiration of the interval 34 to notify the caregiver to reposition the sensor 12. If such visual and/or audible prompts do not result in the sensor 12 being repositioned, more obtrusive signals, such as brighter visual cues or louder audible indicators may be initiated until the sensor 12 is repositioned. Alternatively, if one or more rounds of visual and/or audible prompts do not result in the sensor 12 being repositioned, physiological data derived from the sensor 12 may not be provided (or may be only partially provided) to the caregiver until the sensor 12 is repositioned.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to measurements of blood oxygen saturation, but these techniques may also be utilized for the measurement and/or analysis of other blood or tissue constituents using spectrophotometric principles. For example, using the same, different, or additional wavelengths, the present techniques may be utilized for the measurement and/or analysis of carboxyhemoglobin, met-hemoglobin, total hemoglobin, intravascular dyes, and/or water content.

What is claimed is:

1. A physiological monitoring system, comprising:
   a medical sensor comprising at least one emitter and at least one detector; and
   a physiological monitor comprising a timer set to run for a time interval and at least one of a display or speaker, wherein the timer is configured to start when the physiological monitor receives a signal related to a change in the light received at the at least one detector that is indicative of the medical sensor being affixed to a patient and to reset if the signal indicates that the medical sensor is removed from the patient and reaffixed to the patient prior to the expiration of the time interval and wherein the at least one of a display or a speaker is configured to provide a prompt if the medical sensor is not removed from the patient and reaffixed to the patient during the time interval.

2. The physiological monitoring system of claim 1, wherein the physiological monitor comprises one of a pulse oximetry monitor, a hydration monitor, or a combination thereof.

3. The physiological monitoring system of claim 1, wherein the physiological monitor comprises a multi-parameter monitor.

4. The physiological monitoring system of claim 1, wherein the at least one emitter comprises at least one light emitting diode.

5. The physiological monitoring system of claim 1, wherein the at least one detector comprises a photodetector.

6. The physiological monitoring system of claim 1, wherein the medical sensor comprises at least one of a pulse oximetry sensor, a sensor for measuring a water fraction, or a combination thereof.

7. The physiological monitoring system of claim 1, wherein the medical sensor comprises at least one integrated circuit device.

8. The physiological monitoring system of claim 7, wherein the at least one integrated circuit device is within a cable configured to extend between the medical sensor and the physiological monitor.

9. The physiological monitoring system of claim 1, wherein the timer is configured to start automatically when the signal indicates that the medical sensor is affixed to a patient.

10. The physiological monitoring system of claim 1, wherein the timer is configured to start based upon the signal generated by the at least one detector crossing a predetermined threshold value.

11. The physiological monitoring system of claim 1, wherein the timer is configured to reset based upon the signal related to the change in light and a time interval over which the change occurs.

12. The physiological monitoring system of claim 1, wherein the physiological monitor is configured to provide a visual prompt on the display if the medical sensor is not repositioned during the time interval.

13. The physiological monitoring system of claim 12, wherein the visual prompt comprises a blinking light, an alphanumeric message, or a color code.

14. The physiological monitoring system of claim 1, wherein the physiological monitor is configured to modify a visual indicator of a physiological parameter.

15. The physiological monitoring system of claim 14, wherein modifying the visual indicator comprises at least one of alternating the display of the parameter with non-numeric symbols, employing a different font, employing a different font size, or employing an emphasis technique.

16. The physiological monitoring system of claim 1, wherein the physiological monitor is configured to modify an audible indicator of a physiological parameter.

17. The physiological monitoring system of claim 16, wherein modifying the audible indicator comprises at least one of changing the tone of an audible indicator, turning the audible indicator off, periodically skipping the audible indicator.

18. The physiological monitoring system of claim 1, wherein the physiological monitor is configured to provide an audible prompt via the speaker if the medical sensor is not repositioned during the time interval.

19. The physiological monitoring system of claim 18, wherein the audible prompt comprises an audible alarm or a verbal message.

20. The physiological monitoring system of claim 1, wherein the prompt comprises not displaying at least one physiological parameter on the display.

* * * * *